(12) United States Patent
Chwalisz et al.

(10) Patent No.: US 7,629,334 B1
(45) Date of Patent: Dec. 8, 2009

(54) MESOPROGRESTINS (PROGESTERONE RECEPTOR MODULATIONS) AS A COMPONENT OF COMPOSITIONS FOR HORMONE REPLACEMENT THERAPY (HRT)

(75) Inventors: Kristof Chwalisz, Berlin (DE); Walter Elger, Berlin (DE); Gerd Schubert, Berlin (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 468 days.

(21) Appl. No.: 10/433,984

(22) PCT Filed: Aug. 31, 2000

(86) PCT No.: PCT/US00/23771

§ 371 (c)(1),
(2), (4) Date: Oct. 17, 2003

(87) PCT Pub. No.: WO01/34126

PCT Pub. Date: May 17, 2001

Related U.S. Application Data

(60) Provisional application No. 60/287,546, filed on Aug. 31, 1999.

(51) Int. Cl.
*A61K 31/56* (2006.01)
*C07J 1/00* (2006.01)
*C07J 6/00* (2006.01)

(52) U.S. Cl. ............... 514/170; 514/179; 552/523; 552/553; 552/610

(58) Field of Classification Search ............... 514/170, 514/179; 552/623, 553, 610
See application file for complete search history.

(56) References Cited

U.S. PATENT DOCUMENTS

| | | | |
|---|---|---|---|
| 4,670,426 A | 6/1987 | Zor et al. | |
| 5,468,736 A | 11/1995 | Hodgen | |
| 5,469,836 A | 11/1995 | Greenall | |
| 5,693,628 A | 12/1997 | Schubert et al. | |
| 6,040,340 A | * 3/2000 | Chwalisz et al. | 514/509 |

FOREIGN PATENT DOCUMENTS

| | | | |
|---|---|---|---|
| DE | 4332284 | * | 3/1995 |
| DE | 4332283 A | | 4/1995 |
| DE | 19610635 A | | 9/1997 |
| DE | 19809845 | * | 3/1998 |
| EP | 0648779 A | | 4/1995 |
| WO | WO 93/21926 | | 11/1993 |
| WO | WO 9612494 A | | 5/1996 |
| WO | WO 9749407 A | | 12/1997 |
| WO | WO 9945023 A | | 9/1999 |

OTHER PUBLICATIONS

Jewgenow et al., Comparitive Binding Affinity Study of Progestins to the Cytosol Progestin Receptor of Endometrium in Different Mammals, General and Comparitive Endocrinology 110, 118-124, (1998).*
Fertility and Sterility, 1999 vol. 71(4) Supp 1 Page 95.
Abstract—Schneider B., Exp.Clin. Endocrinol.Diabetes (106, Suppl. 1, S52, 1998).
Bruce A. Lessey, M.D., PhD., Medical management of endometriosis and infertility, Fertility and Sterility, Jun. 2003, vol. 73(6) pp. 1089-1096.

* cited by examiner

*Primary Examiner*—Sreeni Padmanabhan
*Assistant Examiner*—Umamaheswari Ramachandran
(74) *Attorney, Agent, or Firm*—Millen, White, Zelano, Branigan, P.C.

(57) ABSTRACT

The use of mesoprogestins as pharmaceutical components for the manufacture of a medicament for hormone replacement therapy (HRT) and as components for the combined use together with an estrogen for the manufacture of a medicament for HRT as well as in respective HRT-methods and methods of treating hormone deficiency and hormone irregularity symptoms. Mesoprogestins are defined as compounds possessing both agonistic and antagonistic activities at the progesterone receptor (PR) in vivo. They stabilize the function of PR at an intermediate level of agonistic and antagonistic. Corresponding functional states cannot be achieved with progestins or antiprogestins. J867, J912, J956 and J1042 are the mesoprogestins preferred herein.

6 Claims, 2 Drawing Sheets

Figure 1A:
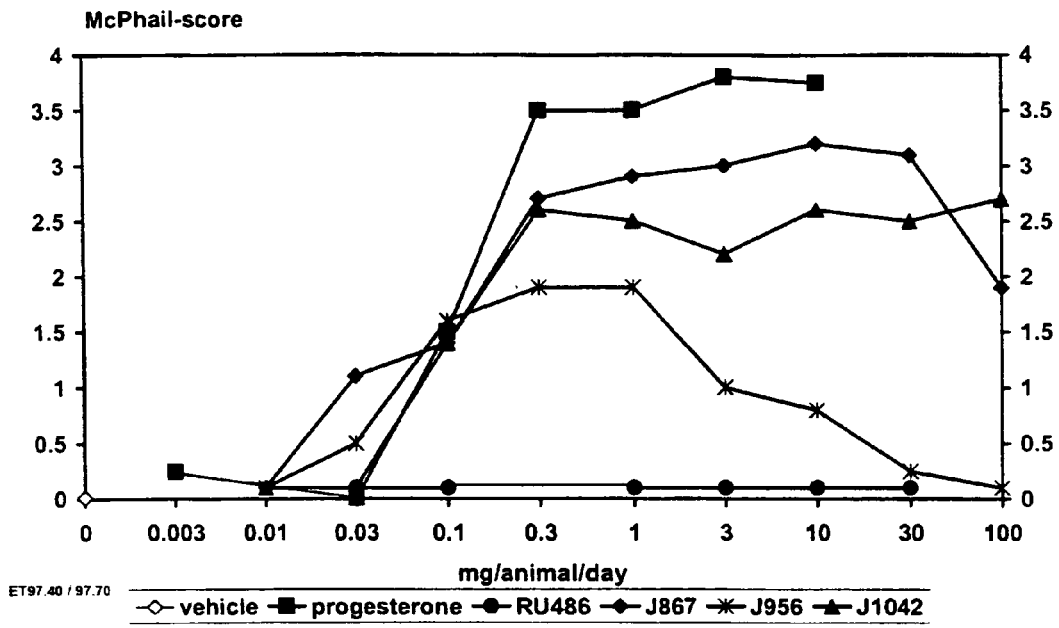

Progesterone-like (above, Fig. 1A) and progesterone antagonistic (below, Fig. 1B) effects of PR-modulators in the uterus of estrogen primed immature rabbits (McPhail test)

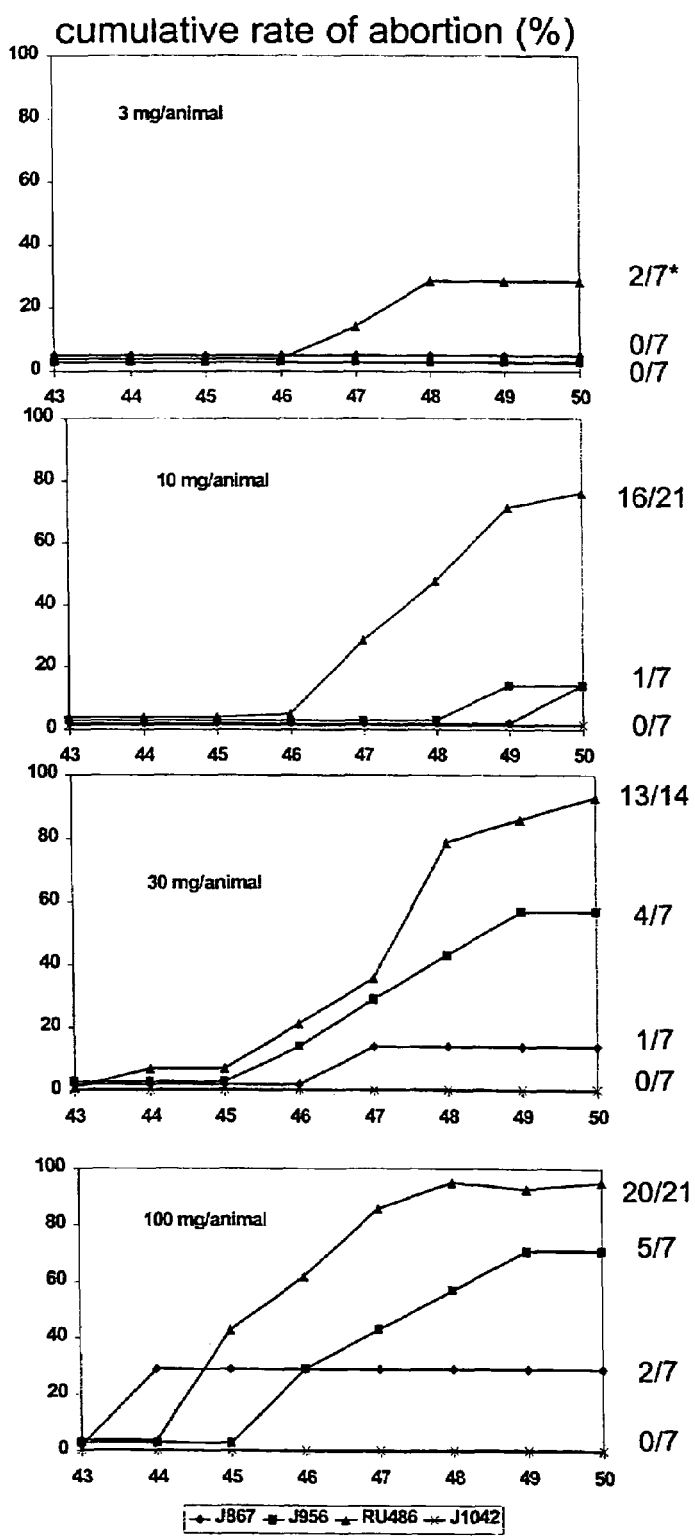
Figure 2: Cumulative rate of abortion until day 50 in guinea pigs treatment on days 43 and 44 of pregnancy by s.c. injection. (#/#) = rate of abortion ns (progesterone receptor modulations) as a component of compositions for hormone replacement therapy (HRT)

This application is a 371 National Phase of PCT/US00/23771 filed Aug. 31, 2000. This application claims the benefit of U.S. Ser. No. 09/386,140 filed Aug. 31, 1999, now converted to U.S. Provisional Application No. 60/287,546, filed Aug. 29, 2000.

The present invention relates to the field of hormone replacement therapy (HRT).

With the onset of menopause in women, so-called menopausal symptoms occur owing to altered hormone production. Because of reduced estrogen production, the risk of osteoporosis increases at the same time (reduction of bone tissue while retaining the same bone structure, due to increased bone degradation and/or reduced bone growth); likewise in postmenopausal women, a myocardial infarction rate that is significantly increased compared to premenopausal women and an increased incidence of other cardiovascular diseases are observed, which also can be attributed to reduced estrogen production.

Hormone replacement therapy (=HRT) with estrogens or with an estrogen/gestagen combination is currently the standard method for treating the symptoms that are associated with menopause (Ernster, V. L. et al. (1988): Benefits and Risks of Menopausal Estrogen and/or Progestin Hormone Use; Prev. Med. 17:201-223).

Estrogen exerts a protective action on the cardiovascular system, on the bones (reduction of the risk of osteoporosis), and on the central nervous system (avoidance of so-called "hot flashes"). However, the chronic use of estrogens in hormone replacement therapy leads to an increased risk of endometrial carcinoma (Ernster, V. L. et al. (1988): Benefits and Risks of Menopausal Estrogen and/or Progestin Hormone Use; Prev. Med. 17:201-223).

By simultaneously using a gestagen for hormone replacement therapy, the stimulating effect of estrogen on the endometrium is suppressed (Gibbson, W. E., 1986, Biochemical and Histologic Effects of Sequential Estrogen/Progestin Therapy on the Endometrium of Postmenopausal Women; Am. J. Obstet. Gynecol: 154:46-61); in contrast, however, in the case of combined therapy with an estrogen and gestagen, the protective effects of the estrogenic components with respect to the plasma lipids can at least be attenuated (Lobo, R. (1992): The Role of Progestins in Hormone Replacement Therapy; Am. J. Obstet. Gynecol. 166: 1997-2004).

In addition, with an estrogen/gestagen treatment based on a hormone dosage that is lower than with an oral contraceptive agent, undesirable intracyclic menstrual bleeding can occur (Hillard, T. C. et al. (1992): Continuous Combined Conjugated Equine Estrogen-Progestagen Therapy: Effects of Medroxyprogesterone Acetate and Norethindrone Acetate on Bleeding Patterns and Endometrial Histologic Diagnosis; Am. J. Obstet. Gynecol. 167: 1-7).

Finally, recent findings show that many gestagens can increase the risk of breast cancer (Staffa, J. A. et al. (1992): Progestins and Breast Cancer: An Epidemiologic Review; 57: 473-491); King, R. J. B. (1991): A Discussion of the Roles of Estrogen and Progestin in Human Mammary Carcinogenesis; J. Ster. Biochem. Molec. Bio. 39: 8111-8118).

In summary, the picture that forms is that the known estrogen-mono- and estrogen/gestagen combination therapies do not represent any satisfactory options for treating the symptoms that are associated with menopause.

Recently, the use of "true" antiestrogens for the production of pharmaceutical agents for hormone replacement therapy (HRT) has also been proposed (EP-A-0 178 862). "True" antiestrogens refer, according to EP-A-0 178 862, for example, to tamoxifen, nafoxidine, MER-25, as well as those antiestrogens which act in a receptor-mediated manner and which at the same time also have an estrogenic (agonistic) partial action. This estrogenic partial action occurs in the uterus and in bone.

A disadvantage to such a pharmaceutical agent that contains a "true" antiestrogen with a partial estrogenic action is that, owing to the chronically estrogenic stimulation of the endometrium, such as occurs with use of estrogens, an increased risk of the development of an endometrial carcinoma exists (Fornander, T. et al. (1989): Adjuvant Tamoxifen in Early Breast Cancer Occurrence of New Primary Cancers: Lancet 21: 117-119).

In contrast, positive effects on the bone are produced by the partial estrogenic action of tamoxifen; in women, tamoxifen seems to partially prevent the degradation of the bone mass (Love, R. R. et al. (1992): Effects of Tamoxifen on Bone Mineral Density in Postmenopausal Women with Breast Cancer; N. Engl. J. Med. 26:852-856).

In addition, studies on tamoxifen have shown that its antiestrogenic component is responsible for growth inhibition when used in the treatment of breast cancer in postmenopausal women (Buckley, M. M. T. et al. (1989); Tamoxifen: A Reappraisal of its Pharmacodynamic and Pharmacokinetic Properties and Therapeutic Use; Drugs 37: 451-490).

In addition, antiestrogens such as raloxifen for inhibiting bone degradation and for treating perimenopausal syndrome have become known (U.S. Pat. No. 5,393,763 or 5,391,557). Antiestrogens of this type show a clearly reduced agonistic (estrogenic) action on the endometrium, but exert a significantly estrogenic action on the bone. Since these substances are also not completely dissociated, however (i.e., they always have a residual estrogenic action on the endometrium), they can also result in a proliferation of the endometrium after long-term treatment.

Accordingly, the necessary chronic use of an antiestrogen with a partial agonistic action in hormone replacement therapy can be considered harmful since stimulation of the endometrium can promote the development of endometrial carcinoma.

WO-EP 94/03408 proposes to avoid this permanent stimulation of the endometrium by simultaneously using a compound with a progesterone-antagonistic action as well as a compound with an antiestrogenic action while at the same time there is a partial agonistic action for the production of a pharmaceutical agent for hormone replacement therapy. In the case of such a pharmaceutical agent, the component with a progesterone-antagonistic action inhibits the changes that are caused by the partial estrogenic action of the antiestrogen (stimulation of the myometrium and endometrium) only in the uterus, while, however, the other estrogenic effects, which are highly desired in hormone replacement therapy, for example on bone and on the cardiovascular system, remain unchanged.

The administration of an estrogen, optionally together with a gestagen, both at very low dosages, which by themselves do not ensure stable bleeding behavior, combined with a periodic, one-time administration of an antiprogestin (progesterone antagonist) for contraception and for hormone replacement therapy, is described in WO-A 93/17686. The progesterone antagonist ensures a reduction in breakthrough bleeding.

The joint, and preferably simultaneous use of a competitive progesterone antagonist with an estrogen without gestagen is described in WO-A 94/18983. The use of the estrogen according to this publication is done entirely according to the conventional principles of estrogen replacement therapy. The progesterone antagonist is used in an amount that inhibits the endometrial proliferation that is induced by estrogen.

WO-A 97/33589 discloses a pharmaceutical agent that contains in combination individual dosage units of an estrogen and individual dosage units of a competitive progesterone antagonist for separate, sequential administration of the competitive progesterone antagonist, which can be used for hormone replacement therapy, as well as packaging that contains this pharmaceutical agent.

In any case, chronic (e.g., daily) treatment with a progesterone antagonist can lead to side-effects, for example in the liver, because of the daily burden of the organism. Moreover, a potential drawback of antiprogestins is that their misuse for abortion cannot be ruled out completely.

It is therefore the object of this invention to provide a pharmaceutical and a method for hormone replacement therapy (HRT) which avoids the aforementioned drawbacks and which provides further favorable features in HRT.

A further object of this invention is to provide application regimens for this pharmaceutical for HRT.

This invention discloses the use of mesoprogestins as pharmaceutical components for the manufacture of a medicament for hormone replacement therapy (HRT).

Another aspect is the combined use of an estrogen together with a mesoprogestin for the manufacture of a medicament for HRT.

A further aspect of the invention is the use of the mesoprogestin in a daily amount of 1.0 to 50.0 mg; more preferred is a daily dose of 5.0 to 25.0 mg mesoprogestin and most preferred is a daily dose of 10.0 to 25.0 mg of a mesoprogestin.

Yet another preferred aspect of the invention is to administer the mesoprogestin in a daily dose to achieve and maintain substantial amenorrhoea due to inhibition of the estrogen-induced endometrial proliferation.

The pharmaceutical agents according to the invention are suitable both for preventive use and for curative use in hormone replacement therapy (HRT), since degradation of bone mass is prevented by the estrogen and simultaneously the estrogen exerts a protective effect on the cardiovascular system and the undesirable stimulating effect on the endometrium is prevented by the antiproliferative action of the mesoprogestin.

These pharmaceutical agents are thus especially suitable for long-term use in HRT.

As mesoprogestins i.a. compounds disclosed in DE 43 32 283 and in DE 43 32 284 are suitable for the purposes of the invention, i.e. as pharmaceutical components for the manufacture of a medicament for hormone replacement therapy (HRT) and as component for the combined use together with an estrogen for the manufacture of a medicament for HRT as well as in respective HRT-methods and methods of treating hormone deficiency and hormone irregularity symptoms in the peri-menopause, the menopause and post-menopause.

As mesoprogestins are preferred the compounds J867, J912, J 900, J 914 and J 956 J 867 [4-[17βMethoxy-17α-(methoxymethyl)-3-oxoestra-4,9-dien-11β-yl]benzaldehyd-(1E)-oxim] and J 912 [4-[17β-Hydroxy-17α-(methoxymethyl)-3-oxoestra-4,9-dien-11β-yl]benzaldehyd-(1E)-oxim] (both DE 43 32 283) and J 900 [4-[17β-Methoxy-17α-(methoxymethyl)-3-oxoestra-4,9-dien-11β-yl]benzaldehyd-(1E)-[O-(ethoxy)carbonyl]oxim], J 914 [4-[17β-Methoxy-17α-(methoxymethyl)-3-oxoestra-4,9-dien-11β-yl]benzaldehyd-(1E)-(O-acetyl)oxim] and J 956 [4-[17β-Methoxy-17α-(methoxymethyl)-3-oxoestra-4,9-dien-11β-yl]benzaldehyd-(1E)-[O-(ethylamino)carbonyl]oxim] (all DE 43 32 284) and J1042 [4-[17β-Methoxy-17α-(methoxymethyl)-3-oxoestra-4,9-dien-11β-yl]benzaldehyd-(1E)-[O-(ethylthio)carbonyl]oxim (German Patent Application 198 09 845.6)].

Further preferred mesoprogestins are

4-[17β-Hydroxy-17α-(ethoxymethyl)-3-oxoestra-4,9-dien-11β-yl]benzaldehyd-(1E)-oxim;

4-[17β-Methoxy-17α-(ethoxymethyl)-3-oxoestra-4,9-dien-11β-yl]benzaldehyd-(1E)-oxim;

4-[17β-Hydroxy-17α-(chloromethyl)-3-oxoestra-4,9-dien-11β-yl]benzaldehyd-(1E)-oxim;

4-[17β-Methoxy-17α-(methoxymethyl)-3-oxoestra-4,9-dien-11β-yl]benzaldehyd-(1E)-(O-methyl)oxim (all DE 43 32 283)

and

4-[17β-Methoxy-17α-(methoxymethyl)-3-oxoestra-4,9-dien-11β-yl]benzaldehyd-(1E)-[O-(phenylamino)carbonyl]oxim;

4-[17β-Methoxy-17α-(methoxymethyl)-3-oxoestra-4,9-dien-11β-yl]benzaldehyd-(1E)-[propionyl]oxim;

4-[17β-Methoxy-17α-(methoxymethyl)-3-oxoestra-4,9-dien-11β-yl]benzaldehyd-(1E)-[benzoyl]oxim (all DE 43 32 284).

J 867 is described in DE 43 32 283 and J 900 and 914 are described in DE 43 32 284 as well as in corresponding patent applications as compounds having strong antiprogestagenic and compared to RU 486 having markedly reduced antiglucocorticoid activity. Moreover these compounds are mentioned to have (indirect) antiestrogenic properties reflected by reduced uterine weights in cyclic guinea pigs.

These effects should promise the exertion of a particularly favorable influence on pathologically modified tissues in which estrogens stimulate growth (endometriotic focuses, myomas, etc.).

The disclosure of these applications does not pertain to the use of the new compounds for hormone replacement therapy.

Also, a progestagenic activity of the compounds which is advantageous for the herein claimed indication HRT is not mentioned in these applications at all.

Further, the mentioned applications are silent about any active dose to be used to treat any of the therein mentioned conditions.

According to the invention mesoprogestins are defined as compounds possessing both agonistic and antagonistic activities at the progesterone receptor (PR) in vivo. As progestins and antiprogestins, mesoprogestins show high binding affinity to PR. However, mesoprogestins exhibit different pharmacodynamic properties compared to either progestins or antiprogestins. The presence of progesterone agonistic activity in mesoprogestins measured in commonly used biological tests in vivo represents the key property of this novel class of PRMs. This activity remains, however, below that of progesterone in the plateau of the dose response curve. Mesoprogestins fail to maintain pregnancy in ovariectomized pregnant rodents as mice and rats.

In the classical bioassay, the McPhail test, assessing progestagenic and antiprogestagenic effects in rabbits (Selye H., Textbook of Endocrinology, 1947, pp. 345-346), progesterone produces a maximum McPhail score of 4 (by definition). Treatment with a mesoprogestin in the absence of progesterone leads, however, to a McPhail score which is higher than that under any dose of RU 486, i.e. above 0.5-1.0, preferentially 2.0-3.0, but to distinctly lower score than 4 at the plateau of the dose response curve at the clinically relevant doses for the claimed indications (i.e. 0.01 mg-30 mg/rabbit).

The capacity of mesoprogestins to antagonize progesterone function is also tested in the McPhail test using a progesterone dose which induces a McPhail score ranging between 3 and 4. A mesoprogestin inhibits the effect of progesterone to a significant degree, but the maximum inhibition is below that which is inducible with RU 486 or other pure antiprogestins (e.g. onapristone).

The mesoprogestins stabilize, therefore, the function of PR at an intermediate activity level providing the rationale for the novel clinical applications in gynecological therapy. Corresponding functional states cannot be achieved with progestins or antiprogestins.

Pharmacological Results Demonstrating the Utility of the Mesoprogestines in the Claimed Indications The PR antagonistic and agonistic properties of mesoprogestins were assessed in estrogen-primed rabbits in the McPhail test according to Selye (Textbook of Endocrinology, 1947, pp. 345-346).

A) Assessment of Pr Agonistic Properties of Mesoprogestins in Rabbits (FIG. 1 A)

The progestagenic activity of J867, J956, J1042 and RU 486 (dose range: 0.003-100 mg/rabbit) was evaluated in estradiol-primed juvenile rabbits after 4 days of subcutaneous (s.c.) treatment in the absence of progesterone). The progestagenic effect of the mesoprogestins was observed at doses equal to or higher that 0.03 mg/rabbit. Progesterone induced endometrial transformation at doses equal to or higher that 0.1 mg reaching a maximum effect at 1 mg/rabbit (approximately McPhail score 4). Neither mesoprogestin tested (J 1042, J867, J956) reached the maximum effect of progesterone. J956 showed a biphasic response in this test with a maximum effect of McPhail score 1.5 at 0.3-1 mg/rabbit.

Figure 1B:
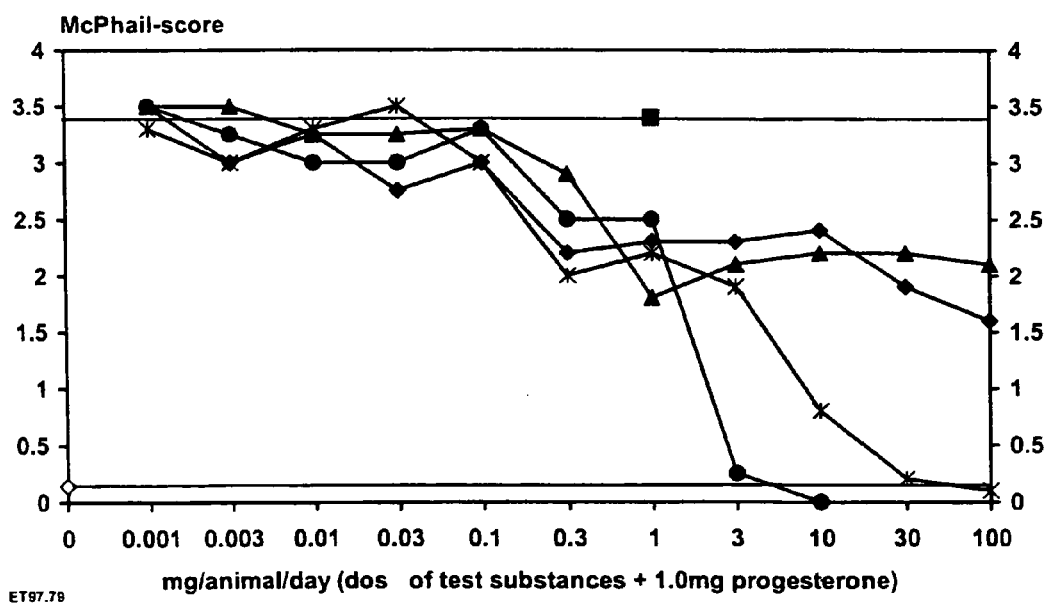

B) Assessment of PR Antagonistic Properties of Mesoprogestins in Rabbits (FIG. 1B)

Similarly, the antiprogestagenic activity of J867, J956, J1042 and RU 486 (dose range: 0.001-100 mg/rabbit) was evaluated in estradiol-primed juvenile rabbits after 4 days of subcutaneous (s.c.) treatment in the presence of progesterone (1 mg/rabbit s.c.). The first antiprogestagenic effect of the mesoprogestins and RU 486 was observed with a dose of 0.3-1 mg mg/rabbit (McPhail index 0=no transformation; 4=complete transformation). The antiprogestagenic activity of mesoprogestins at higher clinically relevant doses (i.e. 3-30 mg/rabbit) was lower that that of RU 486.

In the guinea pig model which allows a good prediction of the effects in humans with respect to the abortifacient activity (Elger W, Beier S., Chwalisz K, Fähnrich M, Hasan S H, Henderson D, Neef G, Rohde R (1986): Studies on the mechanism of action of progesterone antagonists. J Steroid Biochem 25: 835-845) the mesoprogestins J 867, J 912, J 956, J 1042 lead up to 100 mg/kg/day to a maximal abortion rate of 20%.

C) Evaluation of Abortifacient Effects

Physiological Background:

The guinea pig is considered as relevant model of human gestation and parturition (Elger W, Fähnrich M, Beier S, Quing S S, Chwalisz K (1987). Endometrial and myometrial effects of progesterone antagonists in pregnant guinea pigs. Am J Obstet Gynecol 157: 1065-1074; Elger W, Neef G, Beier S, Fähnrich M, Gründel M, Heermann J, Malmendier A, Laurent D, Puri C P, Singh M M, Hasan S H, Becker H (1992). Evaluation of antifertility activities of antigestagens in animal model. In: Puri C P and Van Look P F A (eds), *Current Concepts in Fertility Regulation and Reproduction*. Wiley Eastern Limited, New Delhi, pp. 303-328; Elger W, Faehnrich M, Beier S, Qing S S, Chwalisz K (1986). Mechanism of action of progesterone antagonists in pregnant guinea pigs. *Contraception* 6: 47-62; Elger W, Chwalisz K, Faehnrich M, Hasan S H, Laurent D, Beier S, Ottow E, Neef G, Garfield R E (1990). Studies on labor-conditioning and labor-inducing effects of antiprogesterones in animal model. In: Garfield R E (eds), Norwell, pp. 153-175.) The mechanism of abortion of antiprogestins in this species is the initiation of labor and finally the expulsion of the conceptus. Abortifacient effects in the rat during very early pregnancy reflect inhibitory effects on nidation rather than initiation of uterine contractions. Studies in the rat model lead to "overestimation" of the potential of antiprogestins to terminate pregnancy in humans. Conversely, in the guinea pig model, irrespective of the antiprogestin doses, there were high rates of ongoing pregnancies similar to the situation in humans (Elger et al., *Current Concepts in Fertility Regulation and Reproduction* cited above). Furthermore, in both humans and guinea pigs, there is a strong synergism between antiprogestins and prostaglandins with respect the induction of labor (see the articles cited above and Elger W, Beier S (1983). Prostaglandine und Antigestagene für den Schwangerschaftsabbruch (Prostaglandins and antigestagens for pregnancy termination). German Patent DE 3337450 12; Van Look P, Bygdeman M (1989). Antiprogestational steroids: a new dimension in human fertility regulation. *Oxford reviews of reproductive medicine* 11: 2-60).

Assessment of Labor Inducing Activity: FIG. 2.

Pregnant guinea pigs were treated on days 43 and 44 of pregnancy and observed until day 50 of gestation. For the effects of various treatments see table 1 and FIG. 2. It is typical for this model that expulsions occur with a delay of several days after treatment. It can be seen that Mesoprogestins have a much reduced abortifacient activity compared to RU486. The following ranking of abortifacient activity was found: RU486>J956>J867, J912>J1042. The differences with respect to abortifacient activity seem qualitative ones. It is not possible to overcome the low abortifacient activity of a Mesoprogestin by the use of a higher dose.

TABLE 1

Studies of relative binding activity (RBA) and $ED_{50}$ of abortifacient activity in pregnant rats and guinea pigs.

| Compound | RBA (%) # | | abortifacient activity $ED_{50}$ (mg/animal/day, s.c.) | |
|---|---|---|---|---|
| | PR[1] | GR[2] | Rat[3] | guinea pig[4] |
| RU 486 | 506 | 685 | 0.98* | 3.8 |
| Onapristone | 22 | 39 | 1.71* | ca 3 |
| J867 | 302 | 78 | 0.65* | >100 |
| J956 | 345 | 154 | 0.64* | 20 |
| J912 | 162 | 16 | 0.36 | >100 |
| J1042 | 164 | 42 | >10 | >>100 | by Kaufmann;
[1]progesterone = 100%,
[2]dexamethasone = 100%
[3]treatment days 5-7 of pregnancy, autopsy day 9,
[4]treatment day 43-44 of pregnancy, autopsy day 50,
*SAS, probit procedure.

Application Forms and Regimes of the Estrogens and Mesoprogestins for the Purposes of this Invention:

The estrogenic aspect of this invention is analogous to conventional estrogen replacement therapy. Consequently, any compound that is effective as estrogen can be used in the known doses and according to the methods that are known for estrogen replacement therapy.

As estrogens, all estrogenically active compounds are suitable for the purposes of this invention.

Estrogens that can be used within the scope of this invention are, for example, ethinylestradiol, 17β-estradiol as well as its esters such as estradiol-3-benzoate, estradiol-17-valerate, -cypionate, -undecylate, -enanthate and/or other estradiol esters (U.S. Pat. No. 2,611,773, U.S. Pat. No. 2,990,414, U.S. Pat. No. 2,054,271, U.S. Pat. No. 2,225,419 and U.S. Pat. No. 2,156,599) and conjugated estrogens.

Estradiol-, ethinylestradiol- and estrone-3-sulfamates, for example estrone-N,N-dimethylsulfamate, estrone-N,N-diethylsulfamate, ethinylestradiol-3-N,N-dimethylsulfamate, ethinylestradiol-3-N,N-diethylsulfamate, ethinylestradiol-3-N,N-tetramethylenesulfamate, estrone sulfamate, estradiol-3-sulfamate, estradiol-3-N,N-dimethylsulfamate, estradiol-3-N,N-diethylsulfamate, ethinylestradiol-3-sulfamate, which all represent prodrugs for the corresponding 3-hydroxy compounds (W. Elger et al., in J. Steroid Biochem. Molec. Biol., Vol. 55, No. 3/4, 395-403, 1995; DE 44 29 398 A1 and DE 44 29 397 A1), can also be used in the pharmaceutical agent according to the invention.

Finally, the orally bioavailable derivatives of 17α- and 17β-estradiol with a modified D-ring of the steroid skeleton are also suitable.

The use of a natural estrogen (also conjugated estrogens) or a prodrug of a natural estrogen is preferred according to the invention.

The mesoprogestins can be used analogously as antiprogestins in the HRT-regimes together with an estrogen as is already otherwise disclosed.

Analogously to WO-A 94/18983 both active substances, estrogen and mesoprogestin, are administered simultaneously, either combined or separately, and continuously. This administration can be on a daily basis or in longer regular intervals depending on the release rate of the active substance from its pharmaceutical formulation or depending on the kinetic of the bioavailability of the respective active compound itself.

Another possibility to combine estrogen substitution and mesoprogestin therapy effectively follows the sequential administration regime disclosed for an estrogen/competitive progesterone antagonist-combination in WO-A 97/33589.

According to this regime the dosage units of the estrogen are intended for administration preferably over a period of 28 to 112 days.

In another embodiment the dosage units of the mesoprogestin are provided for administration over a period of at least 4 days and at most 30 days.

A special embodiment contains the dosage units of the mesoprogestin for administration over a period of 7 days.

The pharmaceutical agent is preferably designed in such a way that the dosage units of estrogen and the dosage units of the mesoprogestin are present together in the pharmaceutical agent in such a number that the sum of the number of daily dosage units of the estrogen and the dosage units of the mesoprogestin is 28 or 28 plus 7 or 28 plus a multiple of 7.

The taking of this embodiment of the pharmaceutical agent according to the invention thus leads to an administration cycle that lasts exactly a certain number of weeks, but at least four weeks.

As examples, the following compositions can be used:
28 daily units of estrogen +7 daily units of mesoprogestin, 28 daily units of estrogen +14 daily units of mesoprogestin, 28 daily units of estrogen +21 daily units of mesoprogestin, 56 daily units of estrogen +21 daily units of mesoprogestin, etc.

Compositions of the pharmaceutical agent which are preferred as well are also possible, however, in which the number of the daily dosage units of estrogen and the number of dosage units of the mesoprogestin are not in each case 7 or a multiple of 7: it is important only that the sum of these daily units can be divided by 7, i.e., the taking of the pharmaceutical agent leads to an exactly 4-week or multiple-week administration cycle.

Yet another administration regime for HRT in which a mesoprogestin is used as component starts with the administration of the mesoprogestin alone in the perimenopause. Around the expected occurrence of the menopause an estrogen is administered in addition to the mesoprogestin. Thereafter both components are administered together until the end of the treatment.

Alternatively, a mesoprogestin can be used after the menopause alone, i.e. without an estrogen due to its tissue-specific effects on bones (prevention of osteoporosis) and mammary gland (inhibition of proliferation). Such a regimen may be beneficial for women who do not tolerate estrogens.

This leads to a reliable induction of amenorrhoea already during the perimenopause and guarantees the still required contraception in this stage of life. Otherwise alternative contraceptive measures would be necessary but these would achieve no amenorrhoea.

Perimenopausal women show an increased rate of breakthrough bleeding. This is mainly due to corpus luteum deficiency an inadequate progesterone production. The estrogen production is generally maintained in perimenopausal women. The mesoprogestin is, therefore, administered prior to the menopause in order to stabilize the endometrium. After the menopause, which can be assessed by the measurement of estrogen levels as it is well known to those skilled in the art, the mesoprogestin will be given in combination with an estrogen or a mixture of estrogens.

After the menopause the mesoprogestin cares for the endometrial protection required under the estrogen substitution therapy by suppressing endometrial proliferation. This combination of mesoprogestin and estrogen according to the invention assures induction and maintenance of amenorrhoea during perimenopause.

Again, the administration can be on a daily basis or in longer regular intervals depending on the release rate of the active substance from its pharmaceutical formulation or depending on the kinetic of the bioavailability of the respective active compound itself.

Advantageously in all administration regimes the mesoprogestin is administered in a dose being sufficient to achieve effective amenorrhoea from the beginning of the treatment. Such doses of mesoprogestins being able to induce and maintain amenorrhoea can be determined by routine and conventional methods for instance by determining effectiveness in clinical trials.

Striking advantages of the herein disclosed HRT-methods compared to the classical estrogen/gestagen-HRT-preparations are amenorrhoea from the beginning of the treatment (estrogen/gestagen-preparations are leading to breakthrough bleedings in the first administration cycles and reduced effects on lipid metabolism and mood.

Compared to the regimen containing progesterone antagonists, the mesoprogestins provide a much more balanced endometrial protection due to the inhered partial progestagenic activity. The presence of agonistic activity at the progesterone receptor is beneficial with respect to endometrial protection, i.e. prevention of endometrial hyperplasia due to unopposed estrogen effect on endometrium. Signs of endometrial hyperstimulation were previously described after prolonged treatment of endometriosis with RU 486 (Murphy A A, Kettel L M, Morales A J, et al., (1995) Endometrial effects of long-term, low-dose administration of RU 486, Fertil. Steril. 63: 761-766).

On the other hand, the drawbacks of progestins, i.e. negative effects on lipid metabolism and mood and stimulatory effects on the mammary gland, are reduced or absent during mesoprogestin treatment.

Further, there is no potential for misuse as an abortifacient because of the high doses of a mesoprogestin needed to induce abortion.

According to all embodiments, estrogen can be present in dosage units that are intended for daily administration.

The mesoprogestin can also be present in daily oral dosage units.

If the dosage units of the mesoprogestin are provided for administration over a period of 7 days, these dosage units can advantageously be present in the form of a dosage unit that can be administered once a week.

In such a dosage unit that is to be administered once a week, the mesoprogestin should preferably be prepared in a formulation that results in a delayed release of the active ingredient.

Examples of the following sequential regimen administrations include the following:
  2-3 months estrogen followed by 1-30 days mesoprogestin
  alternate E and mesoprogestin administration, so called 3 day on/off regimen: 3 days estrogen followed by 3 days mesoprogestin, followed by 3 days estrogen, etc. (comment: this progestin/estrogen regimen is currently used in the USA to achieve amenorrhea).

A delayed release of the mesoprogestin can be achieved, for example, by formulating the dosage unit that is to be administered orally as a composite tablet or by providing the dosage unit that is to be administered orally with a timed-disintegration coating, as is readily known to one skilled in the art.

By derivatization, for example by esterification of a free hydroxy group in an effective precursor, the mesoprogestin that is used for the production of the pharmaceutical agent according to the invention can also have a longer half-life than this precursor. As a result, a longer-lasting action is also achieved.

The mesoprogestin is preferably selected for this invention from the group of the compounds J867, J912, J956, J1042.

For the purposes of this invention, the formulation of the estrogen mesoprogestin is done in a completely conventional manner, as is already known for the formulation of these compounds for their individual use in hormone replacement therapy for estrogen, for example Cyclo-Progynova, or as described for J867 in DE 43 32 283.

In particular, reference is also made to the information that is contained in WO-A 93/17686 and WO-A 94/18983.

In addition to oral administration of the estrogen and the mesoprogestin, it is equally possible to administer one or both of the components transdermally, for example with a skin patch, which is best known for the administration of estrogen (Climara Patch).

In addition, administration can be done using an intrauterine release system (c.f. Mirena), but this variant is not preferred within the scope of this invention.

The administration of one or both components as a depot formulation is also possible. Finally, all above-mentioned types of administration can be combined. For example, the estrogen can be administered transdermally with a skin patch, and the progesterone antagonist can be administered daily orally or one or more times as a depot formulation.

The estrogen is contained per daily dosage unit according to the invention in an amount of 1 to 2 mg of 17β-estradiol or a bioequivalent amount of another estrogen.

As bioequivalent amounts of other estrogens for the purposes of this invention, the following amounts can be considered:
  ethinylestradiol 5-35 µg
  conjugated estrogens 0.3- to 1.25 mg.
  In the case of transdermal administration of the estrogen, the transdermal administration system should release daily approximately 50 µg of 17β-estradiol or a bioequivalent amount of another estrogen.
  The administration of the estrogen using a vaginal cream or vaginal ring is also possible. The daily amounts are about 1.25 mg or 0.2 mg in the case of 17β-estradiol. In this case, these are only approximate values.

In the pharmaceutical agent according to the invention, the mesoprogestin is contained in each dosage unit preferably in an amount such that, when used over the intended length of time, it is sufficient for amenorrhea to occur.

In an especially preferred embodiment of the pharmaceutical agent according to the invention, the mesoprogestin is contained in each daily dosage unit in an amount that is equivalent to 0.5 mg to 50 mg, preferably 1 mg to 25 mg of J867.

The bioequivalent doses of a mesoprogestin can be assessed in the McPhail test.

The packaging that contains the pharmaceutical agent according to the invention is prepared in such a way that, in addition to the component(s) mesoprogestin (and estrogen) in the respectively intended form of administration (orally in the form of pills, coated tablets, etc. in a blister pack, as may be appropriate for estrogen and/or progesterone antagonists, or the estrogen as a skin patch and the progesterone antagonist in the form of pills, coated tablets, etc. in a blister or in a capsule as a depot that is to be administered once), said packaging also contains instructions for the use of the pharmaceutical agent (package insert).

The entire disclosure of all applications, patents and publications, cited above or below, and of corresponding provisional application filed as U.S. Ser. No. 09/386,140 on Aug. 31, 1999, and converted to provisional by petition of Aug. 29, 2000 is hereby incorporated by reference.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method for hormone replacement therapy, which comprises administering to a patient in need thereof a pharmaceutical composition comprising a mesoprogestin selected from J867 or J956, wherein the mesoprogestin is the only active agent in the composition and wherein the mesoprogestin is the only active ingredient employed for the hormone replacement therapy method.

2. The method of claim 1, wherein the mesoprogestin is administered in a daily dose amount of from 1.0 mg to 50.0 mg.

3. The method of claim 2, wherein the daily dose amount is from 5.0 mg to 25.0 mg.

4. The method of claim 2, wherein the daily dose amount is from 10.0 mg to 25.0 mg.

5. The method of claim 1, wherein the at least one mesoprogestin is J867.

6. The method of claim 1, wherein the at least one mesoprogestin is J956.

* * * * *

UNITED STATES PATENT AND TRADEMARK OFFICE
CERTIFICATE OF CORRECTION

PATENT NO. : 7,629,334 B1
APPLICATION NO. : 10/433984
DATED : December 8, 2009
INVENTOR(S) : Chwalisz et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1000 days.

Signed and Sealed this

Second Day of November, 2010

David J. Kappos
*Director of the United States Patent and Trademark Office*